United States Patent
Knochel et al.

(10) Patent No.: US 6,191,284 B1
(45) Date of Patent: Feb. 20, 2001

(54) LIGANDS AND COMPLEXES FOR ENANTIOSELECTIVE HYDROGENATION

(75) Inventors: Paul Knochel, Munich (DE); Tanja Ireland, Simiane (FR); Gabriele Grossheimann, Essen (DE); Karlheinz Drauz, Freigericht (DE); Ingo Klement, Pohlheim-Garbenteich (DE)

(73) Assignee: Degussa-Huels Aktiengesellschaft, Frankfurt am Main (DE)

(*) Notice: Under 35 U.S.C. 154(b), the term of this patent shall be extended for 0 days.

(21) Appl. No.: 09/466,936

(22) Filed: Dec. 20, 1999

(30) Foreign Application Priority Data

Dec. 19, 1998 (DE) .............................. 198 58 865
Oct. 30, 1999 (DE) .............................. 199 52 348

(51) Int. Cl.[7] .......................... C07D 207/00; C07F 17/00; B01J 31/00; C07C 5/02
(52) U.S. Cl. .................... 548/402; 556/14; 556/28; 556/136; 556/143; 502/154; 502/155; 585/275
(58) Field of Search .................... 556/14, 28, 136, 556/143; 502/154, 155; 548/402; 585/275

(56) References Cited

U.S. PATENT DOCUMENTS

| | | | |
|---|---|---|---|
| 5,563,309 | * 10/1996 | Togni et al. | 585/277 |
| 5,565,594 | * 10/1996 | Spindler et al. | 556/28 |
| 5,583,241 | * 12/1996 | Spindler | 556/11 |
| 5,912,375 | * 6/1999 | Spindler et al. | 556/14 |
| 5,929,265 | * 7/1999 | Dorta et al. | 556/14 |

* cited by examiner

Primary Examiner—Porfirio Nazario-Gonzalez
(74) Attorney, Agent, or Firm—Oblon, Spivak, McClelland, Maier & Neustadt, P.C.

(57) ABSTRACT

A ferroceneylphosphine ligand and complexes prepared therefrom for homogeneous catalytic enantioselective hydrogenation, the ligand having the formula (I):

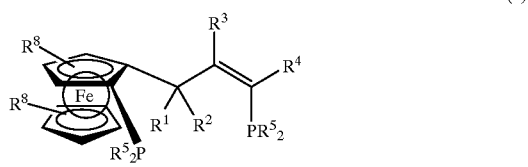

(I)

Another aspect of the invention is directed to a ferroceneylphosphine ligand of formula (II),

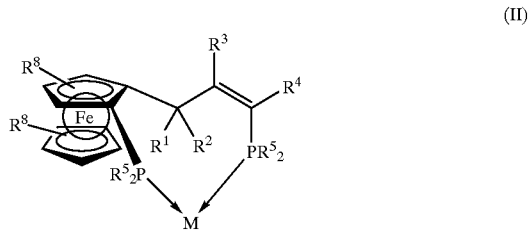

(II)

14 Claims, No Drawings

LIGANDS AND COMPLEXES FOR ENANTIOSELECTIVE HYDROGENATION

BACKGROUND OF THE INVENTION

1. Field of the Invention

The present invention is related to ligands and complexes for homogeneous catalytic enantioselective hydrogenation. More particularly, the invention relates to ligands of formula (I)

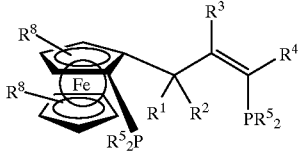

(1)

Another aspect of the invention is related to complexes of formula (II), and to

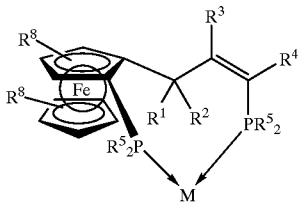

(II)

a method for their preparation and use.

Enantioselective introduction of stereogenic centers into organic molecules by homogeneously catalyzed hydrogenation is established industrially for special applications. The enantioselective products are valuable starting substances for the production of biologically active agents.

2. Discussion of the Background

The use of catalysts containing bisphosphine ligands for enantioselective homogeneous catalytic hydrogenation for the above purposes is known (Burk et al., Tetrahedron, 1994, 4399).

Knochel et al. (Chem. Eur. J. 1988, 4, 950–968), Hayashi et al. (J. Chem. Soc., Chem. Commun. 1989, 495–496) and Ikeda et al. (Tetrahedron Lett. 1996, 4545–4448) describe Pd complexes with $C_2$ symmetric ferrocenyl (bis-tert-phosphine) ligands. However, these complexes were used only in asymmetric allylations.

In contrast, Yamamoto et al. (Bull. Chem. Soc. Jpn. 1980, 53, 1132–1137) reported the use of non-$C_2$-symmetric ferrocenyl(bis-tert-phosphine) ligands in enantioselective homogeneous catalytic hydrogenation reactions. However, only very sporadically good enantiomer excesses are obtained with these ligands.

The basic suitability of non $C_2$ symmetric ferrocenyl ligands for enantioselective hydrogenation is taught in WO 96/32400 and WO 95/21151.

SUMMARY OF THE INVENTION

Accordingly, one object of the present invention is to provide an enantiomer-enriched bisphosphine ligand system and catalysts derived therefrom which are consistently of good effectiveness for the homogeneous enantioselective catalytic hydrogenation of multiple bonds.

Multiple bonds within the scope of the invention are understood to mean double bonds between a carbon atom and another carbon atom or oxygen atom or nitrogen atom.

Briefly, this object and other objects of the present invention as hereinafter will become more readily apparent can be attained by an enantiomer-enriched ligand and salts thereof of formula (I)

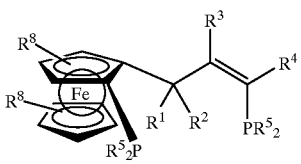

(1)

wherein $R^1$ and $R^2$, independent of one another, are $R^8$, $NR^6R^7$, $SR^6$, ($C_1$–$C_{18}$)-alkyl, ($C_1$–$C_{18}$,)-alkoxy, ($C_2$–$C_{18}$)-alkoxyalkyl, ($C_1$–$C_{18}$)-acyloxy, ($C_6$–$C_{18}$)-aryl, ($C_7$–$C_{19}$)-aralkyl, ($C_3$–$C_{18}$)-heteroaryl, ($C_4$–$C_{19}$)-heteroaralkyl, ($C_1$–$C_8$)-alkyl-($C_6$–$C_{18}$)-aryl, ($C_1$–$C_{19}$)-alkyl-($C_3$–$C_{19}$)-heteroalkyl, ($C_3$–$C_8$)-cycloalkyl, ($C_1$–$C_8$)-alkyl-($C_3$–$C_8$)-cycloalkyl, ($C_3$–$C_8$)-cycloalkyl-($C_1$–$C_8$)-alkyl;

or $R^1$ and $R^2$ are bonded via a ($C_3$–$C_7$)-carbocycle, which is optionally substituted at least once by linear or branched ($C_1$–$C_8$)-alkyl, ($C_1$–$C_8$)-acyl, ($C_1$–$C_8$)-alkoxy, ($C_2$–$C_8$)-alkoxyalkyl and/or optionally contains at least one heteroatom selected from the group consisting of N, O, P and S, in the ring;

$R^3$ and $R^4$, independent of one another, are H, ($C_1$–$C_{18}$)-alkyl, ($C_1$–$C_{18}$)-alkoxy, ($C_2$–$C_{18}$)-alkoxyalkyl, ($C_1$–$C_{18}$)-acyloxy, ($C_6$–$C_{18}$)-aryl, ($C_7$–$C_{19}$)-aralkyl, ($C_3$–$C_{18}$)-heteroaryl, ($C_4$–$C_{19}$)-heteroaralkyl, ($C_1$–$C_8$)-alkyl-($C_6$–$C_{18}$) aryl, ($C_1$–$C_8$)-alkyl-($C_3$–$C_{19}$)-heteroalkyl, ($C_3$–$C_8$)-cycloalkyl, ($C_1$–$C_8$)-alkyl-($C_3$–$C_8$) cycloalkyl and ($C_3$–$C_8$)-cycloalkyl-($C_1$–$C_8$)-alkyl;

or $R^3$ and $R^4$ are bonded via a ($C_3$–$C_5$)-bridge, which optionally contains at least one double bond and/or is optionally substituted at least once by linear or branched ($C_1$–$C_8$)-alkyl, ($C_1$–$C_8$)-acyl, ($C_1$–$C_8$)-alkoxy, ($C_2$–$C_8$)-alkoxyalkyl or optionally contains at least one heteroatom selected from the group consisting of N, O, P and S in the ring;

$R^5$ is ($C_1$–$C_{18}$)-alkyl, ($C_6$–$C_{18}$)-aryl, ($C_3$–$C_8$)-heteroaryl, ($C_1$–$C_8$)-alkyl-($C_6$–$C_{18}$)-aryl, ($C_1$–$C_8$)-alkyl-($C_3$–$C_{19}$)-heteroalkyl, ($C_3$–$C_8$)-cycloalkyl, ($C_1$–$C_8$)-alkyl-($C_3$–$C_8$)-cycloalkyl, where the radical $R^5$ on the same phosphorus atom and/or the two phosphorus atoms can be different;

$R^6$ and $R^7$, independent of one another, are H, ($C_1$–$C_{18}$)-alkyl, ($C_1$–$C_{18}$)-alkoxy, ($C_2$–$C_{18}$)-alkoxyalkyl, ($C_1$–$C_{18}$)-acyl, ($C_6$–$C_{18}$)-aryl, ($C_7$–$C_{19}$)-aralkyl, ($C_3$–$C_{18}$)-heteroaryl, ($C_4$–$C_{19}$)-heteroaralkyl, ($C_1$–$C_8$)-alkyl-($C_6$–$C_{18}$)-aryl, ($C_1$–$C_{18}$)-alkyl-($C_3$–$C_{19}$)-heteroalkyl, ($C_3$–$C_8$)-cycloalkyl, ($C_1$–$C_8$)-alkyl-($C_3$–$C_8$)-cycloalkyl and ($C_3$–$C_8$)-cycloalkyl-($C_1$–$C_8$)-alkyl, or $R^6$ and $R^7$ are bonded via a ($C_3$–$C_7$)-carbocycle, which is optionally substituted at least once by linear or branched ($C_1$–$C_8$) alkyl, ($C_1$–$C_8$) acyl, ($C_1$–$C_8$) alkoxy, ($C_2$–$C_8$)-alkoxyalkyl and/or optionally contains at least one heteroatom selected from the group consisting of N, O, P and S in the ring;

$R^8$ is H or a moiety B-X-Z, where B is a radical selected from the group consisting of $CR^9_2$, $NR^9$, O, S and SiR$^9_2$, X is a spacer selected from the group consisting of 1,4'-biphenyl, 1-,2-ethylene, 1-,3-propylene, PEG-(2-10) and Z is a radical bonded to a polymer via a functional group selected from the group consisting of —O—, —NH—, —CONH, -ethenyl-, —NHCONH—, —OCONH— or —NHCOO—, or the radical R$^8$ of the two cyclopentadienyl rings is bonded via an α,ω-(C$_2$–C$_4$)-alkylene bridge to each other;

R$^9$ is H or (C$_1$–C$_{18}$)-alkyl.

Especially preferred are ligands in which R$^1$, R$^2$, independent of one another, are H, NR$^6$R$^7$, (C$_1$–C$_8$)-alkyl, (C$_1$–C$_8$)-acyloxy, (C$_6$–C$_{18}$)-aryl and (C$_3$–C$_8$)-cycloalkyl;

or R$^1$ and R$^2$ are bonded via a (C$_3$–C$_7$)-carbocycle;

R$^3$ and R$^4$, independent of one another, are (C$_1$–C$_8$)-alkyl, (C$_6$–C$_{18}$)-aryl, (C$_3$–C$_8$)-cycloalkyl;

or R$^3$ and R$^4$ are bonded via a (C$_3$–C$_5$)-bridge, which optionally contains at least one double bond;

R$^5$ is (C$_6$–C$_{18}$)-aryl or (C$_3$–C$_8$)-cycloalkyl,

R$^6$ and R$^7$, independent of one another, are (C$_1$–C$_{18}$)-alkyl, (C$_1$–C$_{18}$)-acyl, (C$_6$–C$_{18}$)-aryl and (C$_3$–C$_8$)-cycloalkyl;

or R$^6$ and R$^7$ are bonded via a (C$_3$–C$_7$)-carbocycle; and

R$^8$ is H.

Another aspect of the invention is an enantiomer-enriched complex of formula (II) and salts thereof;

(II)

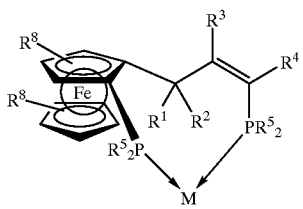

wherein R$^1$ and R$^9$ have the meanings given above and M is a metal atom or ion of subgroup 7 or 8 including Co, Ni, Rh, Ru, Ir, Pd, Re and Pt.

Especially preferred are complexes of formula (II), in which R$^1$ and R$^2$, independent of one another, are H, NR$^6$R$^7$ (C$_1$–C$_8$)-alkyl, (C$_1$–C$_8$)-acyloxy, (C$_6$–C$_8$)-aryl and (C$_3$–C$_8$)-cycloalkyl;

or R$^1$ and R$^2$ are bonded together as a (C$_3$–C$_7$)-carbocycle;

R$^3$ and R$^4$, independent of one another, are (C$_1$–C$_8$)-alkyl, (C$_6$–C$_{18}$)-aryl and (C$_3$–C,)-cycloalkyl;

or R$^3$ and R$^4$ are bonded via a (C$_3$–C$_5$)-bridge, which optionally contains at least one double bond;

R$^5$ is (C$_6$–C$_{18}$)-aryl or (C$_3$–C$_{18}$)-cycloalkyl;

R$^6$ and R$^7$, independent of one another, are (C$_1$–C$_{18}$)-alkyl, (C$_1$–C$_{18}$)-acyl, (C$_6$–C$_{18}$)-aryl and (C$_3$–C$_8$)-cycloalkyl;

or R$^6$ and R$^7$ are bonded via a (C$_3$–C$_7$)-carbocycle; and

R$^8$ is H;

and M is a metal atom or ion of Group 8 such as Rh, Ru or Pd.

A still another aspect of the invention is directed to a method for preparation of the ligands of the invention.

Compounds of formula (III):

(III)

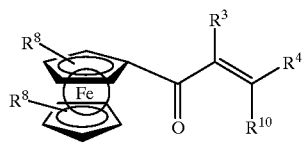

where R$^3$, R$^4$ and R$^8$ are as defined above and R$^{10}$=Hal, can be converted enantioselectively to compounds of formula (IV):

(IV)

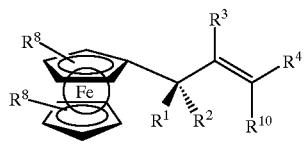

where R$^1$ and R$^2$ are H or OH, where R$^1$ and R$^2$ must not be the same, R$^3$, R$^4$ and R$^8$ have the meanings stated above and R$^{10}$ is Hal.

Then compounds of formula (IV), where R$^1$ and R$^2$ are H or OH, where R$^1$ and R$^2$ must not be the same, R$^3$, R$^4$ and R$^8$ have the meanings stated above and R$^{10}$=H, are converted to compounds of formula (V)

(V)

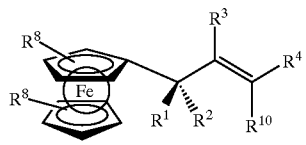

where R$^1$ and R$^2$ are H or N(C$_1$–C$_8$)-alkyl$_2$, where R$^1$ and R$^2$ must not be the same, R$^3$, R$^4$ and R$^8$ have the meanings stated above and R$^{10}$=Hal.

In the next step compounds of formula (V), where R$^1$ and R$^2$ are H or N(C$_1$–C$_8$)-alkyl$_2$, where R$^1$ and R$^2$ must not be the same, R$^3$, R$^4$ and R$^8$ have the meanings stated above and R$^{10}$=Hal, can advantageously be converted to compounds of formula (VI):

(VI)

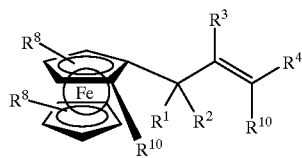

where R$^1$ and R$^2$ are H or N(C$_1$–C$_8$)-alkyl$_2$, where R$^1$ and R$^2$ must not be the same, R$^3$, R$^4$ and R$^8$ can take on the meaning given above, and R$^{10}$=Li.

Finally, compounds of general formula (VI), where R$^1$ and R$^2$ are H or N(C$_1$–C$_8$)-alkyl$_2$, where R$^1$ and R$^2$ must not be the same, R$^3$, R$^4$ and R$^8$ have the meanings stated above and R$^{10}$=Li, can be converted to compounds of formula (I):

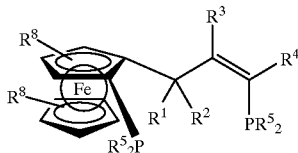

(1)

where $R^1$ and $R^9$ have the meanings described above.

The preparation of the ligand system of the invention can thus take place in a modular fashion, as described in the following scheme.

products are produced in very good yields and with very high optical and diastereometric purity. Another conceivable path for preparation of the desired enantiomer-enriched ligands can take place, for example, by preparing the acylated ferrocenes by means of enantioselective reductive amination. One equally arrives at the enantiomer-enriched ligands with an amine substituent at the stereogenic center in this manner.

Other possibilities for introduction of chirality are described in principle in Tetrahedron Asymmetry 1991, 2, 601–612, J. Org. Chem. 1991, 56, 1670–1672, J. Org. Chem. 1994, 59, 7908–7909, J. Chem. Soc., Chem. Commun. 1990, 888–889.

The enantiomer-enriched alcohols C that are obtained by the above described CBS reaction can now be converted to

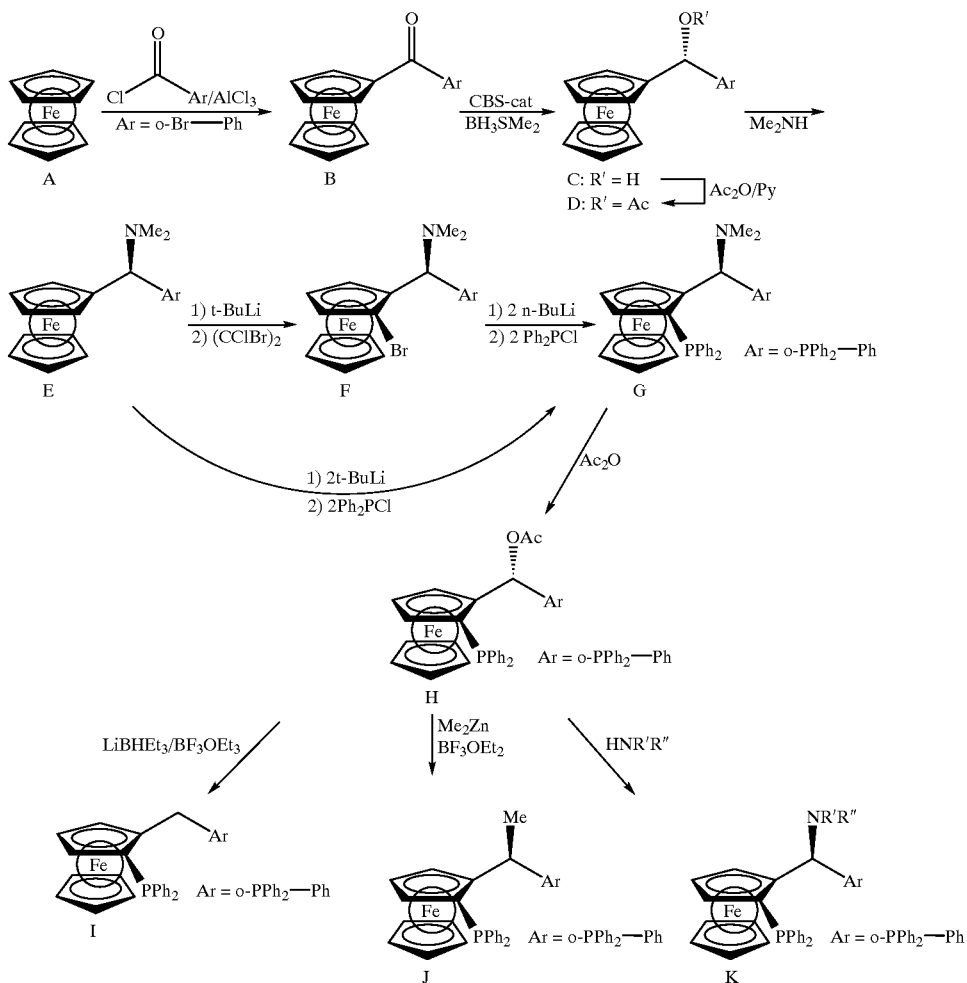

In a first preparation step commercially available ferrocene A is monoacylated under Friedel-Crafts conditions (J. Org. Chem. 1957, 22, 903–906).

For simultaneous insertion of a preferred central and planar chirality the acylated ferrocene B can in principle be converted by any of the methods that are possible to the skilled artisan for this reaction (J. Am. Chem. Soc. 1957, 79, 2742, J. Organometal. Chem. 1973, 52, 407–424). However, reduction with the so-called CBS reagent (J. Am. Chem. Soc. 1987, 109, 5551–5553, Tetrahedron Lett. 1996, 37, 25–28) is preferred. This procedure ensures that the reaction other derivatives of formula E in all of the ways that are known to the skilled artisan. Preferably the derivatives are made by replacing the OH function at the stereogenic center by an amino group. Especially preferred is the preparation of the dialkylamino derivatives, since these can be employed directly for the further conversion to F or via G to H.

In this step the dialkylamino derivatives F can advantageously be deprotonated in the α position at the cyclopentadienyl ring and then reacted with a reagent to introduce a halogen atom, preferably bromine.

The deprotonation reaction can take place with all of the agents that are commonly known to the skilled artisan for this purpose, but preferred is the use of the strong base n-butyllithium (n-BuLi) or t-butyllithium (t-BuLi) in an inert solvent. Preferably the lithium bonded to ferrocene is converted to the brome derivative with $(CCl_2Br)_2$. Because of the chirality present in the molecule, of the two α positions in the ring, one is preferably deprotonated and substituted.

The subsequent introduction of the phosphine groups into the α position of the ferrocene ring and at aromatic compounds occurs advantageously by double halogen-lithium exchange followed by reaction with a phosphine reagent. Preferred possibilities as phosphine reagents are compounds that have a leaving group at the phosphorus atom and thus exhibit electrophilic character. Such reagents are sufficiently well known to the skilled artisan (J. Am. Chem. Soc. 1955, 77, 3526–29). The use of diphenylphosphine chloride is preferred.

The introduction of the phosphine groups can also take place starting from a derivative E. By protonation and halogen-lithium exchange with two equivalents of base, one obtains extremely preferred double lithiated intermediates, which can be converted to G by the above pathway with phosphine groups.

If the radical $R^8$ is not initially present in the starting molecule A, one can subsequently deprotonate the second position possible for deprotonation, the δ position on the ferrocene ring, in another deprotonation experiment like the one just described and then reacted with a suitable electrophilic reagent for introduction of radical $R^8$.

The radical $R^8$ can, among other things, be employed for binding the complexes in accordance with the invention to a polymer matrix such as a linear PMMA, polystyrene or PEG or a nonlinear dendrimer.

The bonding of the radical $R^8$ to the cyclopentadienyl ring of the complex in the invention is altogether quite variable with respect to the free positions on the ring and the rings. Consequently, the introduction of one radical $R^8$ is sufficient. All of the radicals that are known to the skilled artisan as possibilities for this purpose can be used. An appropriate review of molecular enlargement of complex catalysts is provided in Tetrahedron Assymmetry 1998, 9, 691–696. Preferably, radical RW consists of the arrangement B-X-Z, where B is a radical selected from the group consisting of $CR^9{}_2$, $NR^9$, O, S and $SiR^9{}_2$, X is a spacer such as 1,4'-biphenyl, 1- or 2- ethylene, 1- or 3-propylene, PEG-(2-10) and Z is a radical bonded to a polymer like the ones mentioned above, via a functional group such as —O—, —NH—, —COO, —CONH, -ethenyl,-, —NHCONH—, —OCONH— or —NHCOO—. Alternatively, the radicals $R^8$ of the two cyclopentadienyl rings can be bonded to each other via an α-ω-$(C_2-C_4)$-alkylene bridge.

In principle all of the substituent groups needed for the reaction under consideration are present in the molecule. However, the ligand system can be modified by methods known to the skilled artisan in any way, examples of which are pathways I, J and K shown in the scheme above.

Complexes can be prepared from the ligands of the invention by methods known to the skilled artisan. Preferably, however, a complex is prepared just before it is used in a hydrogenation reaction by mixing a ligand and derivative or salt of a transition metal in a reaction solvent.

A desired objective of the invention is to use the ligands of the invention in catalysts for homogeneous enantioselective hydrogenation as well as for catalytic homogeneous enantioselective hydrogenation.

The reactions presented in Table 1 were conducted with ligands 8a–c. The results obtained and the reaction conditions employed are shown in Table 1.

TABLE 1

| No. | Substrate | Conversion, ee value (%) | Ligand and Conditions |
|---|---|---|---|
| | 8a, 8b, 8c structures shown | | |
| 1 | COOR / Ph / N(H)Ac; R = H, Me | quant., 95% ee (with R = Me) | 8a, [Rh]+, MeOH/toluene 1:1, 1 bar, RT, 0.5 h |
| 2 | R, NHCOMe, R'; R = Me, Et; R' = H, CF3 | quant, 76% ee (with R = Et, R' = H) | 8b, [Rh]+, MeOH, 10 bar, RT, 22 h |

TABLE 1-continued
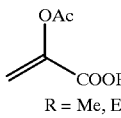
8a    8b    8c
| No. | Substrate | Conversion, ee value (%) | Ligand and Conditions |
|---|---|---|---|
| 3 | 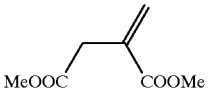<br>R = Me, Et | quant., 72% ee (with R = Me) | 8a, [RH]⁺, MeOH, 5 bar, RT, 22 h |
| 4 | 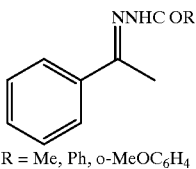 | quant., 91% ee | 8a, [Rh]⁺, MeOH, 1 bar, RT, 14 h |
| 5 | 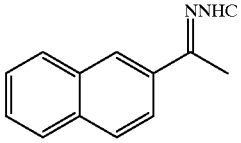<br>R = Me, Ph, o-MeOC₆H₄ | quant., 53% ee (with R = Ph) | 8c, [Rh]⁺, MeOH, 30 bar, RT, 21 h |
| 6 | 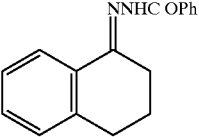 | 95%, 60% ee | 8c, [Rh]⁺, MeOH, 30 bar, RT, 25 h |
| 7 | 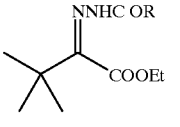 | quant., 63% ee | 8a, [Rh]⁺, MeOH, 30 bar, RT, 10 h |
| 8 | 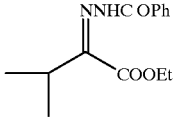<br>R = Me, Ph | 33%, 42% ee (with R = Ph) | 8a, [Rh]⁺, MeOH, 50 bar, RT, 24 h |
| 9 | 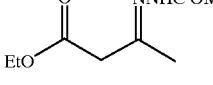 | 23%, 30% ee | 8a, [Rh]⁺, MeOH, 50 bar, RT, 24 h |
| 10 |  | quant., 16% ee | 8a, [Rh]⁺, MeOH, 50 bar, RT, 23 h |

As is clear from Table 1, the present ligand/catalyst system permits various substrates to be hydrogenated with moderate to very good excess amounts of enantiomer.

On top of that, the ligand systems are insensitive to oxidation so that they are storable without alteration for a long time under ambient conditions. This is an advantage for storage in possible industrial applications on a large scale.

Suitable linear or branched ($C_1$–$C_{18}$) alkyl radicals include methyl, ethyl, n-propyl, isopropyl, n-butyl, isobutyl, sec-butyl, tert-butyl, penyl, hexyl, heptyl and octyl up to radicals containing 18 C atoms together with all of their isomers. The radicals ($C_1$–$C_{18}$)-alkoxy include the ($C_1$–$C_{18}$) alkyl radicals with the additional feature that the alkyl radical is bonded via an oxygen atom to the molecule. ($C_2$–$C_8$)-alkoxyalkyl radicals are defined as those in which the alkyl chain is interrupted by at least one oxygen function, where two oxygen atoms cannot be bonded to each other. The number of carbon atoms gives the total number of the carbon atoms present in the residue. The same thing is valid for ($C_1$–$C_8$) alkyl radicals with the stipulation that only a maximum of 8 C atoms can be present in the radical.

The radicals described can be substituted one or more times with halogen and/or radicals that contain N, O, P or S. These are in particular alkyl residues of the above type, which have at least one of these heteroatoms in the chain or which are bonded via one of these heteroatoms to the molecule. The above is correspondingly valid for residues with up to 8 C atoms.

($C_3$–$C_8$)-Cycloalkyl is understood to include cyclopropyl, cyclobutyl, cyclopentyl, cyclohexyl and cycloheptyl residues. The cycloalkyl groups can be substituted with at least one halogen atom and/or N-, O-, P- and S-containing residues and/or can have N-, O-, P-, S-containing radicals in the ring, such as 1-, 2-, 3-, 4-piperidyl, 1-, 2-, 3-, 4-piperidyl, 1-, 2-, 3-pyrrolidinyl, 2- or 3-tetrahydrofuryl, 2-, 3-, 4-morpholinyl.

A ($C_3$–$C_8$)-cycloalkyl-($C_1$–$C_8$)-alkyl radical is one in which the alkyl group and the cycloalkyl group are as defined above, which is bonded to the molecule via one of the alkyl radicals.

($C_1$–$C_{18}$)-Acyloxy is defined as an alkyl residue with a maximum of 18 C atoms which is bonded to the molecule via a COO function. For ($C_1$–$C_8$)-acyloxy the corresponding rule is valid for an alkyl radical containing 8 C atoms.

($C_1$–$C_{18}$)-Acyl is defined as an alkyl radical as defined above with a maximum of 18 C atoms, which is bonded to the molecule via a CO function functional group. For ($C_1$–$C_8$)-acyl the corresponding rule is valid for an alkyl radical containing up to and including 8 C atoms.

A ($C_6$–$C_{18}$)-aryl radical is understood to be an aromatic radical with 6 to 18 carbon atoms. Preferred radicals include phenyl, naphthyl, anthryl, phenanthryl and biphenyl, which optionally are substituted with ($C_1$–$C_8$)-alkoxy, $NR^6R^7$, ($C_1$–$C_8$)-acyl or ($C_1$–$C_8$)-acyloxy.

A ($C_7$–$C_{19}$)-aralkyl radical is a ($C_6$–$C_{18}$) aryl radical bonded to the molecule via a ($C_1$–$C_8$) alkyl residue.

A ($C_3$–$C_{18}$) heteroaryl radical is a five-, six- or seven-member aromatic ring system of 3 to 18 carbon atoms, which contains heteroatoms such as nitrogen, oxygen or sulfur in the ring. Such heteroatoms are in particular radicals such as 1-, 2-, 3-furyl, 1-, 2-, 3-pyrrolyl, 1-, 2-, 3-thienyl, 2-, 3-, 4-pyridyl, 2-, 3-, 4-, 5-, 6-, 7-indolyl, 3-, 4-, 5-pyrazolyl, 2-, 4-, 5-imidazolyl, acrindinyl, quinolinyl, phenanthridinyl, 2-, 4-, 5-, 6-pyrimidinyl.

A ($C_4$–$C_{19}$) heteroaralkyl radical is understood to mean a heteroaromatic system corresponding to the ($C_7$–$C_{19}$) arallkyl residue.

Suitable halogen atoms (Hal) include fluorine, chlorine, bromine and iodine.

Salts are understood to mean ionic addition compounds of strong acids such as HCl, HBr, $H_2SO_4$, $H_3PO_4$, $CF_3COOH$, p-toluenesulfonic acid, methanesulfonic acid and the molecule in question.

PEG means polyethylene glycol.

The term enantiomer enriched is understood, within the scope of the invention, to mean the amount of an enantiomer in a mixture with its optical antipodes in a range of >50% and <100%.

Salts are understood to mean ionic addition compounds of strong acids like HCl, HBr, $H_2SO_4$, $H_3PO_4$, $CF_3COOH$, p-toluenesulfonic acid and methanesulfonic acid and the molecule in question.

The term diastereomer-enriched is understood to mean an excess amount of one diastereomer with respect to one or more other diastereomers.

The complexes and ligands of the invention implies, within the scope of the invention, all possible diastereomers, where the two optical antipodes of a relevant diastereomer are included.

Having now generally described this invention, a further understanding can be obtained by reference to certain specific examples which are provided herein for purposes of illustration only and are not intended to be limiting unless otherwise specified.

EXAMPILES

1) Preparation of ligands

Preparation of o-bromobenzoylferrocene (1)

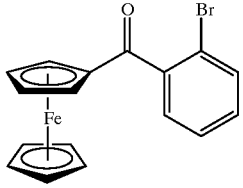

Ferrocene (10.0 g, 53.8 mmol) was dissolved in $CH_2Cl_2$ (50 mL) in a 250 mL round-bottom flask with argon inlet and dripping funnel and cooled to 0° C. Then aluminum (III) chloride (7.88 g. 59.1 mmol) was suspended in $CH_2Cl_2$ (50 mL) in a dropping funnel and o-bromobenzoyl chloride (12.4 g, 7.4 mL, 56.4 mmol) was added dropwise using a syringe. The resulting solution was added by drops of the ferrocene from the dropping funnel. An intense dark purple color appeared. After 2 h of stirring water (15 mL) was slowly added at 0° C. After the end of the hydrolysis, which progressed with strong generation of Gases, the solution was diluted with $CH_2Cl_2$ (100 mL) and washed with potassium carbonate solution (50 mL) and a saturated salt solution (50 mL). The organic phase was dried over magnesium sulfate, filtered and concentrated on a rotary evaporator. The crude product was purified by column chromatography (pentane/tert-butylmethyl ether=4/1). Ketone 1 (16.1 g, 43.6 mmol), 81%) was obtained as a dark red solid (mp: 102° C.).

IR (KBr): 3104 (w), 3092 (w), 1643 (vs), 1447 (m), 1292 (s), 1027 (s), 738 (s).

$^1$H-NMR (CDCl$_3$, 300 MHZ): δ=7.63–7.59 (m, 1H), 7.49–7.46 (m, 1H), 7.40–7.24 (m, 2H), 4.71 (s, 1H), 4.57 (s, 1H), 4.26 (s, 5H).

MS (EI): 370 (M$^{+1}$, 100), 368 (M$^{-1}$, 98), 288 (23), 215 (8), 185 (8).

C$_{17}$H$_{13}$BrFeO (369.05): Calculated: C55.33, H 3.55. Found: C55.26, H 3.53.

Preparation of (R)-(α-hydroxy-o-bromophenylmethyl)ferrocene (2)

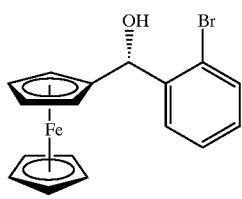

"Methyloxazaborolidine" (EP 305180) (0.90 g, 3.25 mmol, 0.3 eq), dissolved in THF (10 ml,) at 0° C., was placed in a 250 mL round-bottom flask with argon inlet. It was covered with a solution of ketone 1 (4.00 g, 10.80 mmol) in THF (20 mL) or with a borane-dimethyl sulfide complex (1.1 mL, 11 mmol) in THF (11 mL), in each case using a syringe. At first 20% of the borane solution (2.4 mL) was added dropwise, and then stirring was conducted for 5 min. Then the remaining borane solution and the ketone were simultaneously added by drops over a period oft 2 h using a pump. The dark orange colored reaction solution was stirred for another hour after the end of this addition. Then the excess borane was decomposed dropwise with methanol (4 mL). The reaction solution was poured into a saturated ammonium chloride solution (30 mL) and extracted with diethyl ether (50 mL). The organic phase was dried over magnesium sulfate, filtered and concentrated on a rotary evaporator. The crude product was purified by column chromatography (pentane/tert-butylmethyl ether=4/1). Alcohol 2 (3.80 g, 10.26 mmol, 95%, ee=96%) was obtained as an orange solid (mp: 71° C.).

[α]D$^{20}$=–132° (c=1.11, CHCl$_3$)

HPLC (OD, 92% Heptane/8% Isopropanol, 0.6 ml/min): tr=15.9 (R), 18.4 (S).

IR (KBr): 3437 (w), 3096 (s), 2926 (s) 1104 (s), 1292 (s), 1016 (s), 747 (s).

$^1$H-NMR (CDCl$_3$, 300 MHZ): δ=7.65–7.07 (m, 4H), 5.81 (s, 1H), 4.41 (m, 1H), 4.26 (s, 5H), 4.20 (m, 1H), 4.16 (m, 2H), 2.74 (s, 1H).

MS (EI): 372 (M$^{+1}$, 21), 370 (M$^{-1}$, 22), 153 (100), 138 (40).

C$_{17}$H$_{15}$BrFeO (371.05): Calculated: C55.03, H 4.07. Found: C55.86, H 3.95.

Preparation of (R)-(α-acetoxy-o-bromophenylmethyl)ferrocene (3)

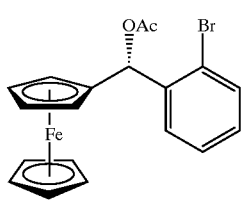

Alcohol 2 (3.5 g, 9.43 mmol) was mixed with pyridine (5 mL) and acetic anhydride (2.5 mL) in a 100 mL round-bottom flask and the solution was stirred for 12 h at room temperature. Volatile substances were removed by an oil pump vacuum. The acetate product 3 (3.90 g, 9.43 mmol) was obtained in quantitative yield as an orange solid (mp: 108° C.).

[α]D$^{20}$=–33.2° (c=1.11, CHCl$_3$)

IR (KBr): 3449 (w), 3098 (w), 1740 (s), 1104 (s), 1222 (s), 1016 (s), 1042 (w), 1012 (w), 750 (s).

$^1$H-NMR (CDCl$_3$, 200 MHZ): δ=7.48–7.36 (m, 2H), 7.21–7.15 (mn, 1H), 7.04–6.97 (m, 1H), 6.96 (s, 1H), 4.17–4.13 (m, 2H), 4.08–4.05 (m, 7H), 2.06 (s, 3H).

MS (EI): 414 (M$^{+1}$, 19), 412 (M$^{-1}$, 20), 180 (95), 153 (100), 121 (18).

C$_{19}$H$_{17}$BrFeO$_2$ (413.05): Calculated: C55.24, H, 4.15. Found: C54.99 H 4.42.

Preparation of (R)-[α-(N,N-dimethylamino)-o-bromophenylmethyl]ferrocene (4)

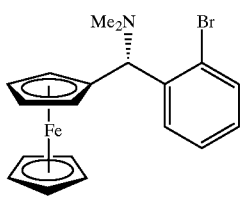

Acetate 3 (3.9 g, 9.43 mmol) was dissolved in acetonitrile (50 mL) and dimethylamine (16 mL, 40% in water) in a 100 mL round-bottom flask and stirred for 12 h at room temperature. The reaction solution was then concentrated on a rotary evaporator, extracted with a diethyl ether and washed with a saturated salt solution. The organic phase was dried over magnesium sulfate, filtered and concentrated on a rotary evaporator. The crude product was purified by column chromatography (pentane/diethyl ether=4/1 up to pure diethyl ether). Amine 4 (3.80 g, 10.26 mmol, 95%) was obtained as an orange solid (mp: 73° C.).

[α]D$^{20}$=–67° C. (c=1.02, CHCl$_3$)

IR (KBr): 3084 (w), 2982 (m), 2939 (m), 2809 (s), 1467 (s), 1201 (mn), 1004 (s), 814 (s), 752 (vs).

$^1$H-NMR (CDCl$_3$, 300 MHZ): δ=7.73–7.70 (mn, 1H), 7.64–7.61 (mn, 1H), 7.39–7.31 (m, 1H), 7.16–7.06 (m, 1H), 4.47 (s, 1H), 4.25–4.24 (in, 1H), 4.20–4.19 (m, 1H), 4.16–4.14 (m, 1H), 4.11–4.09 (in, 1H), 3.76 (s, 5H), 2.07 (s, 6H).

MS (EI): 399 (M$^{+1}$, 62), 397 (M$^{-1}$, 64), 355 (100), 353 (99), 242 (24), 186 (12), 153 (38), 152 (60), 121 (27).

C$_{19}$H$_{20}$BrFeN (398.12): Calculated: C57.32, H 5.06, N 3.52. Found: C57.03, 11 5.37, N 3.43.

Preparation of (R)-[α-(N-pyrrolidinyl)-o-bromphenylmethyl]-ferrocene (5)

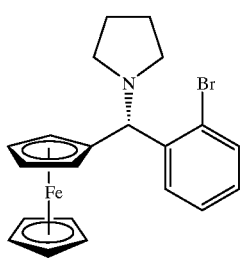

Acetate 3 (0.5 g, 120 mmol) was dissolved in acetonitrile (15 mL), H$_2$O (2.5 mL) and pyrrolidine (0.5 mL, 6 mmol, 5 eq) in a 50 mL round-bottom flask and stirred for 12 h at room temperature. The reaction solution was then concentrated on a rotary evaporator, extracted with diethyl ether and washed with a saturated salt solution. The organic phase was dried over magnesium sulfate, filtered and concentrated on a rotary evaporator. The crude product was purified by column chromatography (pentane/tert-butylmethyl ether=3/1 up to pure tert-butylmethyl ether). Amine 5 (0.48 g, 1.13 mmol, 94%) was obtained as an orange colored solid (mp: 83 CC).

[α]$D^{20}$=−59.7° (c=1.03, CHCl$_3$)

IR (KBr): 2961–2933 (b), 2786 (s), 1106 (s), 820 (s), 747 (s).

$^1$H-NMR (CDCl$_3$, 300 MHZ): δ=7.81–7.78 (m, 1H), 7.64–7.61 (m, 1H), 7.38–7.31 (m, 1H), 7.15–7.12 (m, 1H), 4.49 (s, 1H), 4.25–4.23 (m, 2H), 4.16–4.13 (m, 1H), 4.10–4.08 (m, 1H), 3.84 (s, 5H), 2.37–2.27 (m, 4H), 1.69–1.65 (m, 4H).

MS (EI): 425 ($M^{+1}$, 42), 423 ($M^{-1}$, 45), 355 (93), 353 (100), 268 (44), 152 (87).

$C_{21}H_{22}$BrFeN (424.15): Calculated: C59.47, H 5.23, N 3.30. Found: C59.22, 15.21, N 3.58.

Preparation of 1-[(R)-α-(N,N-dimethylamino)-o-bromophenylmethyl]-2-[(S)-bromo]ferrocene (6)

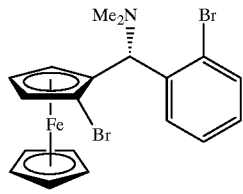

Amine 4 (0.270 g, 0.68 mmol) was dissolved in diethyl ether (3 mL) in a 25 mL round-bottom flask and cooled to −78° C. Then t-BuLi (1.45M in pentane, 1.65 mL, 2.39 mmol, 3.5 eq) was slowly added to the reaction mixture dropwise. The reaction solution was heated to room temperature and stirred for another hour. Finally a solution of $C_2Br_2Cl_4$ (0.487 g, 1.49 mmol, 2.2 eq.) in diethyl ether (2 mL) at −78° C. was added by drops and the mixture was stored for 2 h at room temperature. The reaction solution was extracted with diethyl ether (15 mL) and washed with saturated salt solution. The organic phase was dried over magnesium sulfate, filtered, and concentrated on a rotary evaporator. The crude product was purified by column chromatography (pentane/diethyl ether=511). Amine 6 (0.26 g, 0.54 mmol, 80%, ee=97.5%) was obtained as an orange solid (mp: 84° C.).

[α]$D^{20}$=+125.5 (c=0.71, CHCl$_3$)

HPLC (OJ, 95% Heptane/5% Isopropanol, 0.6 ml/min): tr=7.1 (1R, 2S), 10.6 (1S, 2R)

$^1$H-NMR (CDCl$_3$, 300 MHZ): δ=7.56–7.54 (m, 114), 7.20–7.18 (m, 2H), 7.07–7.00 (m, 1H), 5.06 (s, 1H), 4.47–4.46 (m, 1H), 4.37–4.36 (in, 1H), 4.18–4.13 (m, 1H), 4.12 (s, 5F1), 2.43 (s, 6H).

MS (EI): 479 ($M^{+2}$, 30), 478 ($M^{+1}$, 12), 477 ($M^+$, 61), 475 ($M^{-2}$, 33), 435 (17), 433 (36), 431 (18), 322 (14), 320 (15), 212 (74), 152 (100).

$C_{19}H_{19}Br_2$FeN (477.01): Calculated: C47.84, H 4.01, N 2.94. Found: C47.72, H 3.94, N 2.79.

Preparation of 1-(o-bromophenylmethyl)-2-[(S)-bromo]ferrocene (7)

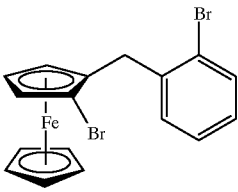

Amine 6 (0.295 g, 0.62 mmol) was dissolved in trifluoroacetic acid (2 mL) in a 25 mL round-bottom flask and triethylsilane (1 mL, 6.20 mmol, 10 eq.) was added dropwise. The reaction solution was stirred for 72 h and then extracted with diethyl ether, washed and saturated aqueous $K_2CO_3$ solution with a saturated salt solution. The organic phase was dried over magnesium sulfate, filtered and concentrated on a rotary evaporator. The crude product was purified by column chromatography (pentane/diethyl ether=20/1). The product 7 (0.152 g, 0.35 mmol, 57% ee=97%) was obtained as an orange oil.

[α]$D^{20}$=+28.5 (c=1.04, CHCl$_3$)

HPLC (OJ, 98% heptane/2% isopropanol, 0.6 ml/min): tr=12,8 (1R, 2S), 15.6 (1S, 2R).

IR (KBr): 3094 (b), 2926 (m), 1470 (m),1439 (m), 1107 (n), 1024 (s), 821 (s), 740 (s).

$^1$H-NMR (CDCl$_3$, 300 MHZ): δ=7.56–7.53 (m, 1H), 7.21–7.16 (m, 1H), 7.11–7.04 (m,2H), 4.45 (m, 1H), 4.20 (s, 5H), 4.15 (m, 1H), 4.09 (m, 1H), 3.93 (m, 2H).

MS (EI): 436 ($M^{+2}$, 24), 435 ($M^{+1}$, 14), 434 ($M^+$, 44), 432 ($M^{-2}$, 25) 217 (22),152 (100).

$C_{17}H_{14}Br_2$FeN (433.94): Calculated: C47.05, H 3.25. Found: C47.31, H 3.45.

Preparation of 1-[(o-(diphenylphosphine)phenylmethyl]-2-[(S)-diphlenylphosphino]ferrocene (8)

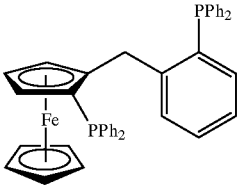

Compound 7 (0.120 g, 0.27 mmol) was dissolved in THF (2 mL) in a 10 mL round-bottom flask and cooled to −78° C. Then n-BuLi (1.6 M in hexane, 0.37 mL, 0.59 mmol, 2.2 eq.) was added dropwise at −78° C. The reaction solution was stirred for 15 min and then ClPPh$_2$ (0.12 mL, 0.66 mmol, 2.4 eq.) was added by drops. After 2 h of stirring at room temperature the solution was extracted with diethyl ether (10 mL) and washed with water and a saturated salt solution. The organic phase was dried with magnesium sulfate, filtered and concentrated on a rotary evaporator. The crude product was purified by column chromatography (pentane/diethyl) ether=20/1). The disphosphine 8 (0.130 g, 0.20 mmol, 75%) was obtained as an orange solid.

[a]$D^{20}$=+46.4° (c=0.59, CHCl$_3$)

$^1$H-NMR (CDCl$_3$, 300 MHZ): δ=7.55–7.48 (m, 2H), 7.26–7.03 (m, 19H), 6.86–6.85 (m, 2H), 6.67–6.64 (m, 1H), 4.19–4.18 (m, 1H), 4.10–4.05 (m, 31H), 3.86 (s, 5H), 3.65 (s, 1H).

$^{13}$C-NMR (CDCl$_3$, 75 MHZ): δ=145.6 (d, J=25 Hz), 139.3–126.0 (m), 93.3 (d, J=25 Hz), 75.4 (m), 72.7, 70.8, 69.8, 68.9, 33.1 (m).

$^{13}$C-NMR (CDCl$_3$, 81 MHZ): δ=−13.6 (d, J=5.7 Hz), −21.9 (d, J=5.7 Hz).

MS (EI): 645 (M$^{+1}$, 46), 644 (M$^+$, 56), 579 (27), 459 (100), 392 (44), 337 (65), 183 (70).

C$_{41}$H$_{34}$FeP$_2$ (644.50): HRMS: Calculated: 644.1485. Found: 644.1478.

Preparation of 1-[(R)-[α-(N,N-dimethlamino)]-o-(diphenylphosphino)phenylmethyl]-2-[(S)-diphenyiphosphino]ferrocene (9)

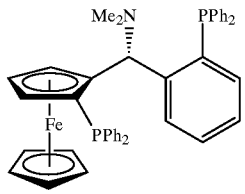

Amine 4 (0.502 o, 1.26 mmol) was dissolved in diethyl ether (5 mL) in a 25 mL round-bottom flask with argon inlet and cooled to −78° C. Then t-BuLi (1.45M in pentane, 3.05 mL, 4.41 mmol, 3.5 eq.) was slowly added dropwise. The reaction solution was stirred at −78° C. for 10 min and heated to room temperature and stirred for another hour. Then, ClPPh$_2$ (0.58 mL, 3.15 mmol, 2.5 eq.) at −78° C. was added dropwise and was stirred for 2 h at room temperature after warming the mixture. The reaction solution was extracted with CH$_2$Cl$_2$ (15 mL) and washed with a saturated salt solution. The organic phase was dried over magnesium sulfate, filtered and concentrated on a rotary evaporator. The crude product was purified by column chromatography (pentane/diethyl ether=5/1). Diphosphine 9 (0.763 g, 1.11 mmol, 88%) was obtained as an orange solid (mp: 84° C.).

[α]D$^{20}$=+297° (c=1.06, CHCl$_3$)

IR (KBr): 3442 (w), 3067 (m), 2776 (m), 1432 (s), 742 (s), 689 (vs).

$^1$H-NMR (CDCl$_3$, 300 MHZ): δ=7.52–7.42 (mn, 2H), 7.32–6.66 (m, 22H), 6.12–5.92 (m, 1H), 4.55 (s, 1H), 4.28 (s, 1H), 3.87 (s, 1H), 3.82 (s, 5H), 2.02 (s, 6H).

$^{13}$C-NMR (CDCl$_3$, 50 MHZ): δ=146.9 (d, J=24.3 Hz), 139.5–126.4 (m), 98.5 (d, J=24.7 Hz), 73.2 (m), 71.5 (d, J=4.5 Hz), 71.2 (d, J=5.4 Hz), 70.1, 68.6, 64.5–64.1 (m), 43.2.

$^{13}$P-NMR (CDCl$_3$, 81 MHZ): δ=−16.7 (d. J=19.1 Hz), −23.2 (d, J=19.1 Hz).

MS (EI): 688 (M$^{+1}$, 23), 687 (M$^+$, 37), 673 (23), 672 (40), 643 (33), 621 (43), 502 (67), 459 (73), 337 (100), 183 (94).

C$_4$H$_{39}$FeNP, (687.57): Calculated: C75.11, H 5.72, N 2.04. Found: C74.87, H5.64, N 1.97.

Preparation of 1-[(R)-[α-(N-pyrrolidino)-o-(diphenylphosphino)phenylmethyl]-2-[(S)-diphenylphosphino]ferrocene (10)

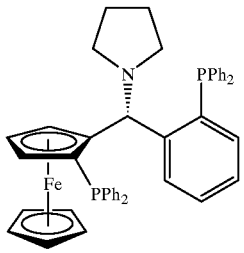

Amine 5 (0.335 g, 0.81 mmol) was dissolved in diethyl ether (15 mL) in a 50 mL round-bottom flask with argon inlet and cooled to −78° C. Then t-BuLi (1.45 M in pentane, 1.96 mL, 2.84 mmol, 3.5 eq.) was slowly added dropwise. The reaction solution was stirred at −78° C. for 10 min and heated to room temperature and stirred for another hour. Finally, ClPPh$_2$ (0.37 mL, 2.02 mmol, 2.5 eq.) at −78° C. was added dropwise and was stirred for 2 h at room temperature after warming the mixture. The reaction solution was extracted with CH$_2$Cl$_2$ (15 mL) and washed with a saturated salt solution. The organic phase was dried over maganesium sulfate, filtered and concentrated on a rotary evaporator. The crude product was purified by column chromatography (pentane/diethyl ether=5/1). Diphosphine 10 (0.370 g, 0.52 mmol, 64%) was obtained as an orange solid (mp: 94° C.).

[α]D$^{20}$ =+232° (c=1.14, CHCl$_3$)

IR (KBr): 3458 (w), 3050 (m), 2962 (m), 2871 (s), 1432 (s), 742 (vs), 689 (vs).

$^1$H-NMR (CDCl$_3$, 300 MHZ): δ=7.72–7.64 (m, 1H), 7.59–7.52 (m, 2H), 7.37–6.76 (m, 2H), 6.10–5.84 (mn, 1H), 4.62–4.52 (mn, 1H), 4.30 (s, 1H), 3.92 (s, 1H), 3), 3.78 (s, 5H), 2.50–2.32 (mn, 4H), 1.38–1.10 (mn, 4H).

$^{13}$C-NMR (CDCl$_3$, 75 MHZ): δ=148.6 (d, J=25 Hz), 139.4–126.1 (m), 98.8 (d, J=23 Hz), 76.4, 72.4 (d, J=14.9 Hz), 71.1 (m), 69.7, 68.1, 62.5 (mn), 51.5, 22.9.

$^{13}$C-NMR (CDCl$_3$, 81 MHZ): δ=−17.1 (d, J=20.3 Hz), −22.4 (d, J=20.3 Hz).

MS (EI): 714 (M$^{+1}$, 22), 713 (M$^+$, 62), 656 (36), 528 (18), 459 (100), 337 (63), 183 (36).

C$_{45}$H$_{41}$FeNP$_2$ (713.60): Calculated: C75.74, H 5.79, N 1.96. Found: C74.61, H 5.97, N 1.68.

HRMS: Calculated: 713.2064; Found: 713.2083

2) Reactions with the ligands/complexes

Typical procedure for hydrogenation in a Schlenk vessel with H$_2$ cylinder.

0.01 mmol [Rh(nbd)$_2$]BF$_4$ (0.0037 g, 1.0 eq.) was weighed into a 50 mL Schlenk vessel with 1.05–1.10 eq. of the corresponding ferrocenyl ligand, evacuated and aerated with argon three times and then dissolved in 4 mL of the given solvent. After about 30 min the orange colored solution was mixed with a solution of 1.0 mmol of the corresponding substrate (100 eq) in 4 mL solvent. The reaction solution was briefly evacuated and the H$_2$ cylinder was connected, whereupon a deepening of the color began very quickly. In some cases it was possible to observe a second change of color to orange brown, which indicated the end of the reaction. After the given reaction time the H$_2$ cylinder was disconnected, the solution was concentrated to about one third of its volume, filtered over diatomaceous earth and evaporated completely. The conversion was determined by $^1$H NMR.

A typical procedure for hydrogenation in an autoclave 0.01 mmol [Rh(nbd)$_2$BF$_4$ (0.0037 g, 1.0 eq.) was weighed into a Schlenk vessel with 1.05–1.10 eq. of the corresponding ferrocene ligand, evacuated and aerated with oxygen three times and then dissolved in 4 mL of the given solvent. The substrate (1.00 mmol. 100 eq.) was weighed into the glass insert of the autoclave, the autoclave was screwed shut, evacuated and aerated with argon three times. (If the substrate that is used is highly volatile, it was added to the catalyst solution about 30 min afterward and the empty autoclave was evacuated and filled with argon). The catalyst solution was fed to the autoclave using a syringe and the Schlenk vessel was washed with 4 mL solvent. The autoclave was sealed, charged with 5–10 bar H$_2$ three times and the given pressure was established. In reactions that were not conducted at room temperature, heating (or cooling) was first conducted to the desired temperature and then the pressure was established. After the given reaction time the hydrogen was released and the reaction mixture was completely evaporated. The residue was dissolved in ether (or in the case of an incomplete reaction in ether/methanol), filtered through silica gel and again concentrated by evaporation. The conversion was determined by means of $^1$H NMR.

Results, see Table 1.

Item 1, table:

3-Phenyl-2-acylamidopropanoic acid methyl ester:

The enantiomer excess was determined by means of GC (Chirasil-Val, 140° C., isothermally: $t_R$/min=10.1 (R), 11.7 (S)).

3-Phenyl-2-acylamidopropanoic acid:

The crude product was dissolved in a mixture of 5 mL methanol 5 mL ether and carefully mixed with 1.0 mL trimethylsilyldiazomethane (2.0 mol in hexane). After 2 h all volatile components were removed and the conversion and enantiomer excess were determined as described above.

Item 2, table:

Preparation of the enamides and analytical data of the hydrogenation products by analogy with literature methods.

Item 3, table:

Preparation of enol esters and analytical data of hydrogenation products by analogy with literature methods.

Item 4, table:

Dimethyl itaconate, Aldrich Company, analytical data of hydrogenation product by analogy with literature methods.

Items 5 and 6, table:

Preparation of acetophenone-N-benzoylhydrazone and 1-(2-naphthyl)ethyl-N-benizoylhydrazone and analytical data of hydrogenation products by analogy with literature methods.

1-Phenyl-1-(2-acetylhydrazone)ethane:

HPLC (OJ, 30° C., 5% iPrOH, 0.8 mL/min): $t_R$/min=15.4, 18.7

1-Phenyl-1-(2-p-methoxybenzoylhydrazino)ethane:

HPLC (OJ, 30° C., 10% iPrOH, 0.5 mL/min): $t_R$/min= 27.9 (S), 30.8 (R)

Item 7, Table:

1-Tetralone-N-benzoylhydrazone:

A suspension of 8.46 g benzoylhydrazine (62 mmol) and 10.0 mL α-tetralone (62 mmol) in 80 mL THF was mixed with 4 drops of concentrated HCl, whereupon a pale yellow solution immediately resulted. After 24 h the solution was concentrated to about ½ of its volume and diluted with ether. The precipitated colorless solid was removed by filtration, washed two times with 10 mL THF and three times with 20 mL ether. Yield: 7.63 g colorless solid, another 8.40 g could be isolated by further processing of the mother liquor (61 mmol, 98%).

IR (KBr): 3204 (m), 3063 (m), 3005 (m), 2925 (m), 1654 (s), 1639 (s), 1537 (s), 1283 (s), 1136 (m), 763 (m), 713 (mn), 694 (m)

$^1$H-NMR (CDCl$_3$, 300 MHZ): δ=9.10 (br s, 1H), 8.40–7.80 (m, 3H), 7.60–7.40 (m, 3H), 7.30–7.10 (m, 3H) 2.79 (t, J=6.1 Hz, 2H), 2.66 (t, J=6.5 Hz, 2H), 1.97 (m, 2H)

$^{13}$C-NMR (CDCl$_3$, 75 MHZ): δ=139.8, 131.7, 129.6, 128.4, 126.6, 125.3, 29.4,25.1, 21.7

MS (EI, 70 eV): m/z=264.1260 (M$^+$, 14%, C$_{17}$H$_{16}$N$_2$O Calculated: 264.1263), 148 (24), 105 (100), 77 (42)

1-Tetralone-N-benzoylhydrazine:

HPLC (OD, 40° C., 10% iPrOH, 0.6 mL/min): $t_R$/min= 16.9, 22.5

$^1$H-NMR (CDCl$_3$, 200 MHZ): δ=7.93 (br s, 1H), 7.80–7.70 (m, 2H), 7.60–7.30 (m, 5H), 7.20–7.00 (m, 2H), 4.90 (br s, 1H), 4.11 (t, J=3.7 Hz, 1H), 2.80–2.60 (m, 2H), 2.10–1.95 (m, 2H), 1.80–1.60 (m,2H).

$^{13}$C-NMR (CDCl$_3$, 75 MHZ): δ=167.5, 138.0, 135.4, 132.7, 131.7, 129.6, 129.0, 128.5, 127.4, 126.7, 125.9, 57.5, 29.2,26.8, 18.0

Item 8, 1Table:

Preparation of hydrazone by analogy with literature methods.

2-Acetylhydrazino-3,3-dimethylbutanoic acid ethyl ester:

HPLC (OD, 40° C., 13% iPrOH, 0.8 mL/min): $t_R$/min= 7.0, 10.1

2-Benzoylhydrazino-3,3-dimethylbutanoic acid ethyl ester:

HPLC (OD, 30° C., 3% iPrOH, 0.8 ml,/min): $t_R$/min= 20.3, 23.9

Item 9, Table

2-Benzoylhydrazino-3-methylbutanoic acid ethyl ester:

HPLC (OD, 20° C., 5% iPrOH, 0.6 mL/min): $t_R$/min= 20.1, 23.8

Item 10, Table:

Preparation of hydrazone by analogy with literature methods.

3-Acetylhydrazinobutanoic acid ethyl ester:

HPLC (AD, 30° C., 4% iPrOH, 0.6 mL/min): $t_R$/min= 39.6, 43.5

The disclosures of German priority Application Number 198 58 865.8 and Application Number 199 52 348.7 each filed Dec. 19, 1998 are hereby incorporated by reference into the present application.

Obviously, numerous modifications and variations of the present invention are possible in light of the above teachings. It is, therefore, to be understood that within the scope of the appended claims, the invention may be practiced otherwise than as specifically described herein.

What is claimed as new and is intended to be secured by Letters Patent is:

1. An enantiomer-enriched ligand of formula (I) and salts thereof:

(1)

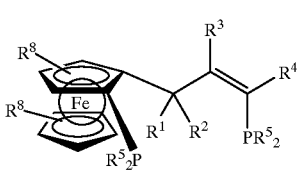

wherein R$^1$ and R$^2$, independent of one another, are R$^8$, NR$^6$R$^7$, SR$^6$, (C$_1$–C$_{18}$)-alkyl, (C$_1$–C$_{18}$)-alkoxy, (C$_2$–C$_{18}$)-alkoxylalkyl, (C$_1$–C$_{18}$)-acyloxy, (C$_6$–C$_{18}$)-aryl, (C$_7$–C$_{19}$)-aralkyl, (C$_3$–C$_{18}$)-heteroaryl, (C$_4$–C$_{19}$)- heteroaralkyl, $(C_1-C_8)$-alkyl-$(C_6-C_{18})$-aryl, $(C_1-C_8)$-alkyl-$(C_3-C_{19})$-heteroalkyl, $(C_3-C_8)$-cycloalkyl, $(C_1-C_8)$-alkyl-$(C_3-C_8)$-cycloalkyl, $(C_3-C_8)$-cycloalkyl-$(C_1-C_8)$-alkyl;

or $R^1$ and $R^2$ are bonded via a $(C_3-C_7)$ carbocycle, which can be substituted one or more times by linear or branched $(C_1-C_1,)$-alkyl, $(C_1-C_8)$-acyl, $(C_1-C_8)$-alkoxy, $(C_2-C_8)$-alkoxyalkyl and/or can contain heteroatoms like N, O, P, S in the ring;

$R^3$ and $R^4$, independ of one another, are H, $(C_1-C_{18})$-alkyl, $(C_1-C_{18})$-alkoxy, $(C_2-C_{18})$-alkoxylalkyl, $(C_1-C_{18})$-acyloxy, $(C_6-C_{18})$-aryl, $(C_7-C_{19})$-aralkyl, $(C_3-C_{18})$-heteroaryl, $(C_4-C_{19})$-heteroaralkyl, $(C_1-C_8)$-alkyl-$(C_6-C_{18})$-aryl, $(C_1-C_8)$-alkyl-$(C_3-C_{19})$-heteroalkyl, $(C_3-C_8)$-cycloalkyl, $(C_1-C_8)$-alkyl-$(C_3-C_8)$-cycloalkyl, $(C_3-C_8)$-cycloalkyl-$(C_1-C_8)$-alkyl;

or $R^3$ and $R^4$ are bonded via a $(C_3-C_5)$ bridge, optionally containing at least one double bond and/or optionally substituted by at least once by linear or branched $(C_1-C_8)$-alkyl, $(C_1-C_8)$-acyl, $(C_1-C_8)$-alkoxy, $(C_2-C_8)$-alkoxyalkyl and/or optionally contains at least one heteroatom selected from the group consisting of N, O, P and S in the ring;

$R^5$ is $(C_1-C_{18})$-alkyl, $(C_6-C_{18})$-aryl, $(C_3-C_{18})$-heteroaryl, $(C_1-C_8)$-alkyl-$(C_6-C_{18})$-aryl, $(C_1-C_8)$-alkyl-$(C_3-C_{19})$-heteroalkyl, $(C_3-C_8)$-cycloalkyl, $(C_1-C_8)$-alkyl-$(C_3-C_8)$-cycloalkyl, where the residues $R^5$ on the same phosphorus atom and/or the two phosphorus atoms can be different;

$R^6$ and $R^7$, independent of one another, are H, $(C_1-C_{18})$-alkyl, $(C_1-C_8)$-alkoxy, $(C_2-C_8)$-alkoxylalkyl, $(C_1-C_8)$-acyl, $(C_6-C_{18})$-aryl, $(C_7-C_{19})$-aralkyl, $(C_3-C_{18})$-heteroaryl, $(C_4-C_{19})$-heteroaralkyl, $(C_1-C_8)$-alkyl-$(C_6-C_{18})$-alkyl, $(C_1-C_8)$-alkyl-$(C_3-C_{19})$-heteroalkyl, $(C_3-C_8)$-cycloalkyl, $(C_1-C_8)$-alkyl $(C_3-C_8)$-cycloalkyl, $(C_3-C_8)$-cycloalkyl-$(C_1-C_8)$-alkyl;

or $R^6$ and $R^7$ are bonded via a $(C_3-C_7)$ carbocycle, which optionally is substituted at least once by linear or branched $(C_1-C_8)$-alkyl, $(C_1-C_8)$-acyl, $(C_1-C_8)$-alkoxy, $(C_2-C_8)$-alkoxyalkyl and/or the carbocycle optionally containing at least one heteroatom selected from the group consisting of N, O, P and S in the ring;

$R^8$ is H or a radical B-X-Z, wherein B is a radical selected from the group consisting of $CR^9_2$, $NR^9$, O, S or $SiR^9_2$, X is a spacer selected from the group consisting of 1,4'-biphenyl, 1- or 2-ethylene, 1- or 3-propylene and PEG-(2-10) and Z is a radical bonded to a polymer via a functional group selected from the group consisting of O—, NH—, COO—, CONH, ethenyl, NHCONH—, OCONH— and NHCOO—;

or the residues $R^8$ of the two cyclopentadienyl rings are bonded to each other via an $\alpha,\omega$-$(C_2-C_4)$-alkylene bridge; and $R^9$ is H or $(C_1-C_{18})$-alkyl.

2. The compound as claimed in claim 1, wherein $R^1$ and $R^2$, independent of one another, are H, $NR^6R^7$, $(C_1-C_8)$-alkyl, $(C_1-C_8)$-acyloxy, $(C_6-C_{18})$-aryl and $(C_3-C_8)$-cycloalkyl;

or $R^1$ and $R^2$ are bonded via a $(C_3-C_7)$-carbocycle;

$R^3$ and $R^4$, independent of one another, are $(C_1-C_8)$-alkyl, $(C_6-C_{18})$-aryl and $(C_3-C_8)$-cycloalkyl;

or $R^3$ and $R^4$ are bonded via a $(C_3-C_5)$-bridge, which optionally contains at least one double bond;

$R^5$ is $(C_6-C_{18})$-aryl or $(C_3-C_8)$-cycloalkyl;

$R^6$ and $R^7$, independent of one another, are $(C_1-C_{18})$-alkyl, $(C_1-C_{18})$-acyl, $(C_6-C_{18})$-aryl and $(C_3-C_8)$ cycloalkyl;

or $R^6$ and $R^7$ are bonded via a $(C_3-C_7)$-carbocycle, $R^8$ is H.

3. An enantiomer enriched complex of formula (II) and salts thereof:

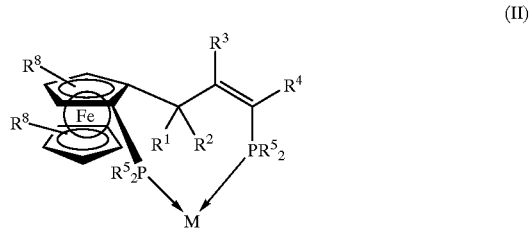

(II)

$R^1$ and $R^2$, independent of one another, are $R^8$, $NR^6R^7$, $SR^6$, $(C_1-C_{18})$-alkyl, $(C_1-C_{18})$-alkoxy, $(C_2-C_{18})$-alkoxylalkyl, $(C_1-C_{18})$-acyloxy, $(C_6-C_{18})$-aryl, $(C_7-C_{19})$-aralkyl, $(C_3-C_{18})$-heteroaryl, $(C_4-C_{19})$-heteroaralkyl, $(C_1-C_8)$-alkyl-$(C_6-C_{18})$-aryl, $(C_1-C_8)$-alkyl-$(C_3-C_{19})$-heteroalkyl, $(C_3-C_8)$-cycloalkyl, $(C_1-C_8)$-alkyl-$(C_3-C_8)$-cycloalkyl and $(C_3-C_8)$-cycloalkyl-$(C_1-C_8)$-alkyl;

or $R^1$ and $R^2$ are bonded via a $(C_3-C_7)$ carbocycle, which is optionally substituted at least once by linear or branched $(C_1-C_8)$-alkyl, $(C_1-C_8)$-acyl, $(C_1-C_8)$-alkoxy, $(C_2-C_8)$-alkoxyalkyl and/or optionally contains at least one heteroatom selected from the group consisting of N, O, P and S in the ring;

$R^3$ and $R^4$, independent of one another, are H, $(C_1-C_{18})$-alkyl, $(C_1-C_{18})$-alkoxy, $(C_2-C_{18})$-alkoxyalkyl, $(C_1-C_{18})$-acyloxy, $(C_6-C_{18})$-aryl, $(C_7-C_{19})$-aralkyl, $(C_3-C_{18})$-heteroaryl, $(C_4-C_{19})$-heteroaralkyl, $(C_1-C_8)$-alkyl-$(C_6-C_{18})$ aryl, $(C_1-C_8)$-alkyl-$(C_3-C_{19})$-heteroalkyl, $(C_3-C_{18})$-cycloalkyl, $(C_1-C_8)$-alkyl-$(C_3-C_8)$-cycloalkyl and $(C_3-C,)$-cycloalkyl-$(C_1-C_8)$ alkyl;

or $R^3$ and $R^4$ are bonded via a $(C_3-C_5)$-bridge, which optionally contains at least one double bond and/or optionally is substituted at least once by linear or branched $(C_1-C_8)$-alkyl, $(C_1-C_8)$-acyl, $(C_1-C_8)$-alkoxy, $(C_2-C_8)$-alkoxyalkyl and/or optionally contains at least one heteroatom selected from the group consisting of N, O, P and S in the ring;

$R^5$ is $(C_1-C_{18})$-alkyl, $(C_6-C_{18})$-aryl, $(C_3-C_{18})$-heteroaryl, $(C_1-C_8)$-alkyl-$(C_6-C_{18})$-aryl; $(C_1-C_8)$-alkyl-$(C_3-C_{19})$ heteroalkyl, $(C_3-C_8)$ cycloalkyl or $(C_1-C_8)$-alkyl-$(C_3-C_8)$-cycloalkyl, where the radicals $R^5$ on the same phosphorus atom and/or the two phosphorus atoms optionally are different;

$R^6$ and $R^7$, independent of one another, are H, $(C_1-C_{18})$-alkyl, $(C_1-C_{18})$-alkoxy, $(C_2-C_{18})$-alkoxylalkyl, $(C_1-C_{18})$-acyl, $(C_6-C_{18})$-aryl, $(C_7-C_{19})$-aralkyl, $(C_3-C_{18})$-heteroaryl, $(C_4-C_{19})$-heteroaralkyl, $(C_1-C_8)$-alkyl-$(C_6-C_{18})$-aryl, $(C_1-C_8)$-alkyl-$(C_3-C_{19})$-heteroalkyl, $(C_3-C_8)$-cycloalkyl, $(C_1-C,)$-alkyl-$(C_3-C_8)$-cycloalkyl or $(C_3-C_8)$-cycloalkyl-$(C_1-C_8)$-alkyl;

or $R^6$ and $R^7$ are bonded via a $(C_3-C_7)$-carbocycle, which optionally is substituted at least once by linear or branched $(C_1-C_8)$-alkyl, $(C_1-C_8)$-acyl, $(C_1-C_8)$-alkoxy, $(C_2-C_8)$-alkoxyalkyl and/or optionally contains at least one heteroatom selected from the group consisting of N, O, P and S in the ring;

$R^8$ is H or a radical B-X-Z, where B is a radical selected from the group consisting of $CR^9_2$, $NR^9$, O, S and $SiR^9_2$, X is a spacer selected from the group consisting of 1,4'-biphenyl, 1- or 2-ethylene, 1- or 3-propylene and PEG-(2-10) and Z is a radical bonded to a polymer via a functional group selected from the group consisting of —O—, —NH—, —COO—, —CONH, -ethenyl, —NHCONH—, —OCONH— or —NHCOO—;

or the radicals $R^8$ of the two cyclopentadienyl rings are bonded to each other via an $\alpha,\omega$-$(C_2-C_4)$-alkylene bridge, $R^9$ is H or $(C_1-C_{18})$ alkyl, and M is a metal atom or ion selected from the group consisting of Co, Ni, Rh, Ru, Ir, Pd, Re and Pt.

4. The enantiomer-enriched ligand as claimed claim 3, wherein $R^1$ and $R^2$, independent of one another, are H, $NR^6R^7$, $(C_1-C_8)$-alkyl, $(C_1-C_8)$-acyloxy, $(C_6-C_8)$-aryl and $(C_3-C_8)$-cycloalkyl;

or $R^1$ and $R^2$ are bonded via a $(C_3-C_7)$-carbocycle;

$R^3$ and $R^4$, independent of one another, are $(C_1-C_8)$-alkyl, $(C_6-C_{18})$-aryl and $(C_3-C_8)$-cycloalkyl;

or $R^3$ and $R^4$ are bonded via a $(C_3-C_5)$ bridge, which optionally contains at least one double bond;

$R^5$ is $(C_6-C_{18})$-aryl or $(C_3-C_8)$-cycloalkyl;

$R^6$ and $R^7$, independent of one another, are $(C_1-C_{18})$-alkyl, $(C_1-C_{18})$-acyl, $(C_6-C_{18})$-aryl are $(C_3-C_8)$-cycloalkyl;

or $R^6$ and $R^7$ are bonded via a $(C_3-C_7)$-carbocycle, $R^8$ is H, and M is a metal atom or ion selected from the group consisting of Rh, Ru and Pd.

5. A method for preparation of ligands as claimed in claim 1, comprising:

enantioselectively converting the compounds of formula (III)

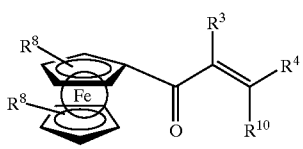

(III)

where $R^3$, $R^4$ and RI have the meanings stated above and $R^{10}$=Hal, into compounds of formula (IV):

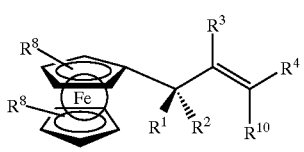

(IV)

where $R^1$, $R^2$ are H or OH, where $R^1$ and $R^2$ must not be the same, $R^3$, $R^4$ and $R^8$ have the meanings stated above and $R^{10}$=Hal.

6. A method for preparation of ligands as claimed in claim 2, comprising:

enantioselectively converting the compounds of formula (III)

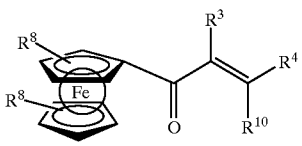

(III)

where $R^3$, $R^4$ and $R^8$ have the meanings stated above and $R^{10}$=Hal, into compounds of formula (IV):

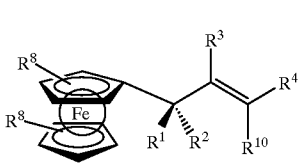

(IV)

where $R^1$, $R^2$ are H or OH, where $R^1$ and $R^2$ must not be the same, $R^3$, $R^4$ and $R^8$ have the meanings stated above and $R^{10}$=Hal.

7. The method as claimed in claim 5, wherein the compounds of formula (IV), where $R^1$, $R^2$ are H or OH, where $R^1$ and $R^2$ must not be the same, $R^3$, $R^4$ and $R^8$ have the meanings stated above and $R^{10}$=Hal, are converted to compounds of formula (V)

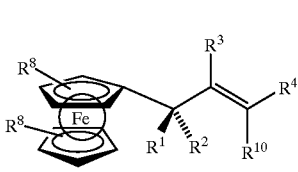

(V)

where $R^1$ and $R^2$ are H or $N(C_1-C_8)$-alkyl$_2$, where $R^1$ and $R^2$ must not be the same, $R^3$, $R^4$ and $R^8$ have the meanings stated above and $R^{10}$ means Hal.

8. The method as in claim 7, wherein the compounds of formula (V), where $R^1$, $R^2$ are H or OH, where $R^1$ and $R^2$ must not be the same, $R^3$, $R^4$ and $R^8$ have the meanings stated above and $R^{10}$=Hal, are converted to compounds of formula (VI)

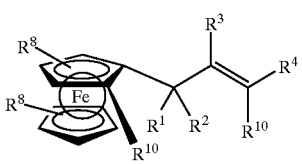

(VI)

where $R^1$ and $R^2$ are H or $N(C_1-C_8)$-alkyl$_2$, where $R^1$ and $R^2$ must not be the same, $R^3$, $R^4$ and $R^8$ have the meanings stated above and $R^{10}$=Li.

9. The method as in claim 8, wherein the compounds of formula (VI), where $R^1$ and $R^2$ are H or $N(C_1-C_8)$-alkyl$_2$, where $R^1$ and $R^2$ must not be the same, $R^3$, $R^4$ and $R^8$ have the meanings stated above and $R^{10}$=Li, are converted to compounds of formula (I)

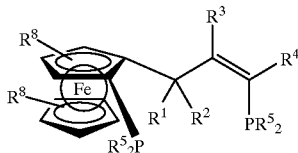

(1)

where $R^1$ to $R^9$ have the meanings stated in claim 1.

10. The method as claimed in claim 6, wherein the compounds of formula (IV), where $R^1$, $R^2$ are H or OH, where $R^1$ and $R^2$ must not be the same, $R^3$, $R^4$ and $R^8$ have the meanings stated above and $R^{10}$=Hal, are converted to compounds of formula (V)

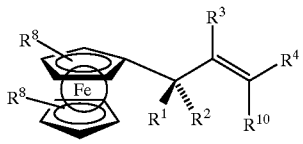

(V)

where $R^1$ and $R^2$ are H or $N(C_1$–$C_8)$-alkyl$_2$, where $R^1$ and $R^2$ must not be the same, $R^3$, $R^4$ and $R^8$ have the meanings stated above and $R^{10}$ means Hal.

11. The method as in claim 10, wherein the compounds of formula (V), where $R^1$, $R^2$ are H or OH, where $R^1$ and $R^2$ must not be the same, $R^3$, $R^4$ and $R^8$ have the meanings stated above and $R^{10}$=Hal, are converted to compounds of formula (VI)

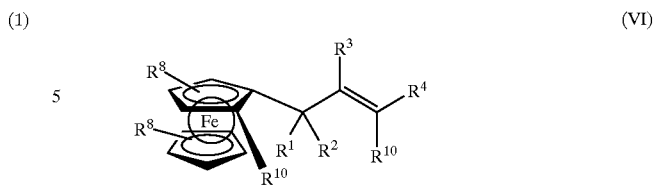

(VI)

where $R^1$ and $R^2$ are H or $N(C_1$–$C_8)$-alkyl$_2$, where $R^1$ and $R^2$ must not be the same, $R^3$, $R^4$ and $R^8$ have the meanings stated above and $R^{10}$=Li.

12. The method as in claim 11, wherein the compounds of formula (VI), where $R^1$ and $R^2$ are H or $N(C_1$–$C_8)$-alkyl$_2$, where $R^1$ and $R^2$ must not be the same, $R^3$, $R^4$ and $R^8$ have the meanings stated above and $R^{10}$=Li, are converted to compounds of formula (I)

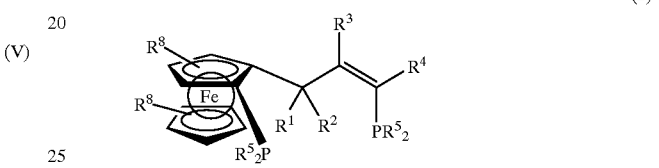

(1)

where $R^1$ to $R^9$ have the meanings stated in claim 1.

13. A method of homogeneous enantioselective hydrogenation, comprising:
  conducting homogeneous enantioselective hydrogenation of a substrate with a complex metal catalyst containing the ligand of claim 1.

14. A method of homogeneous enantioselective hydrogenation, comprising:
  conducting homogeneous enantioselective hydrogenation of a substrate with the complex metal catalyst of claim 3.

* * * * *